(12) United States Patent
Witowski

(10) Patent No.: US 7,806,861 B2
(45) Date of Patent: Oct. 5, 2010

(54) CLOSURE PIECE FOR MEDICAL SYRINGE

(75) Inventor: Norbert Witowski, Wolfenbüttel (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 12/092,343

(22) PCT Filed: Oct. 31, 2006

(86) PCT No.: PCT/EP2006/010879

§ 371 (c)(1),
(2), (4) Date: Sep. 22, 2008

(87) PCT Pub. No.: WO2007/051655

PCT Pub. Date: May 10, 2007

(65) Prior Publication Data

US 2009/0082725 A1 Mar. 26, 2009

(30) Foreign Application Priority Data

Nov. 2, 2005 (DE) .................. 10 2005 052 545

(51) Int. Cl.
*A61M 5/00* (2006.01)
*A61M 5/32* (2006.01)

(52) U.S. Cl. .................... 604/111; 604/192
(58) Field of Classification Search ............ 604/111, 604/192
See application file for complete search history.

(56) References Cited

U.S. PATENT DOCUMENTS

| | | | |
|---|---|---|---|
| 5,135,496 A * | 8/1992 | Vetter et al. ............ 604/111 |
| 5,624,402 A | 4/1997 | Imbert | |
| 6,491,665 B1 | 12/2002 | Vetter et al. | |
| 2006/0178627 A1 | 8/2006 | Geiger et al. | |

FOREIGN PATENT DOCUMENTS

| | | |
|---|---|---|
| DE | 199 56 243 A1 | 5/2000 |
| DE | 199 09 824 A1 | 9/2000 |
| EP | 0 716 860 A2 | 6/1996 |
| EP | 1 600 190 A1 | 11/2005 |

* cited by examiner

*Primary Examiner*—Nicholas D Lucchesi
*Assistant Examiner*—Rebecca E Eisenberg
(74) *Attorney, Agent, or Firm*—Millen, White, Zelano & Branigan, P.C.

(57) ABSTRACT

A closure piece (1) for a medical syringe is provided, the syringe having a syringe barrel (3) and a syringe neck (23). The closure piece has an adapter (6) which can be fitted onto the syringe neck (23). A screw-type closure piece (4) can be fitted onto the adapter (6). A twist-off ring (13) is connected to the screw-type closure piece (4). A closure cap (5) can be introduced into the syringe neck (23).

7 Claims, 3 Drawing Sheets

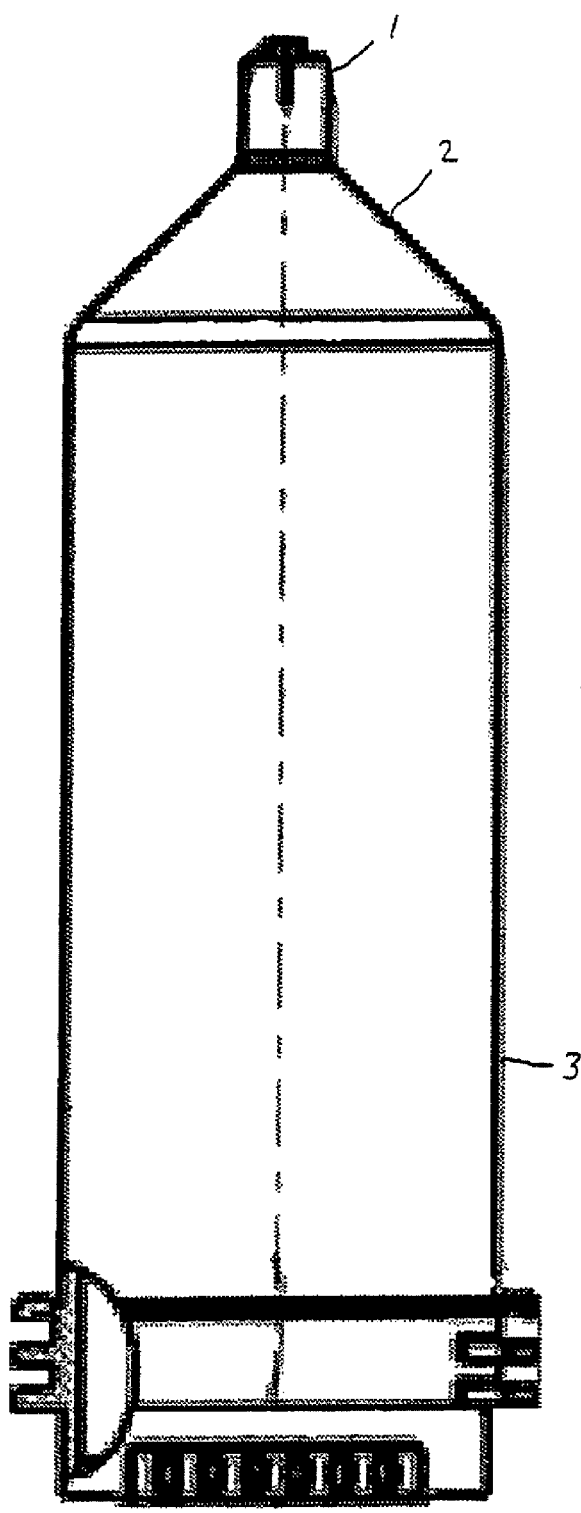
FIG..1
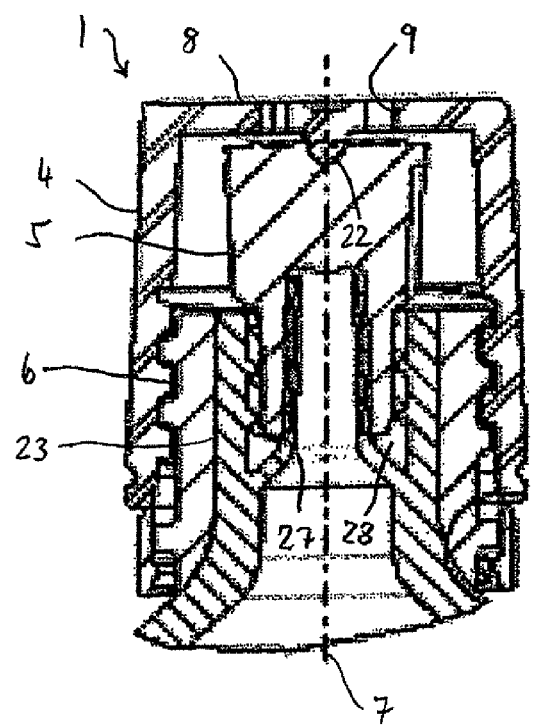
FIG..2

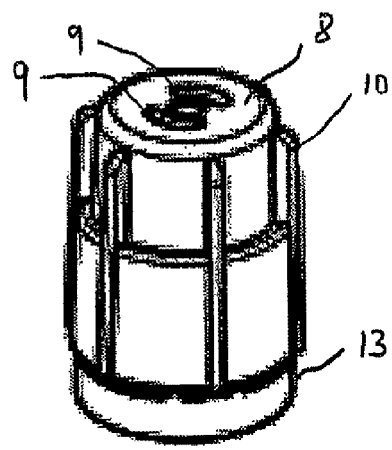
FIG..3
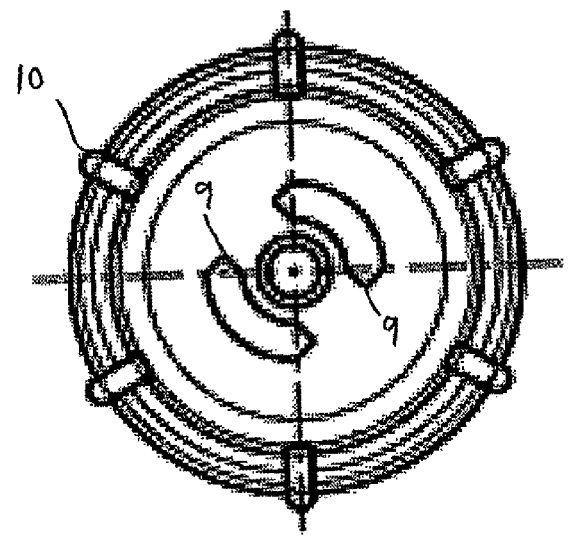
FIG..4
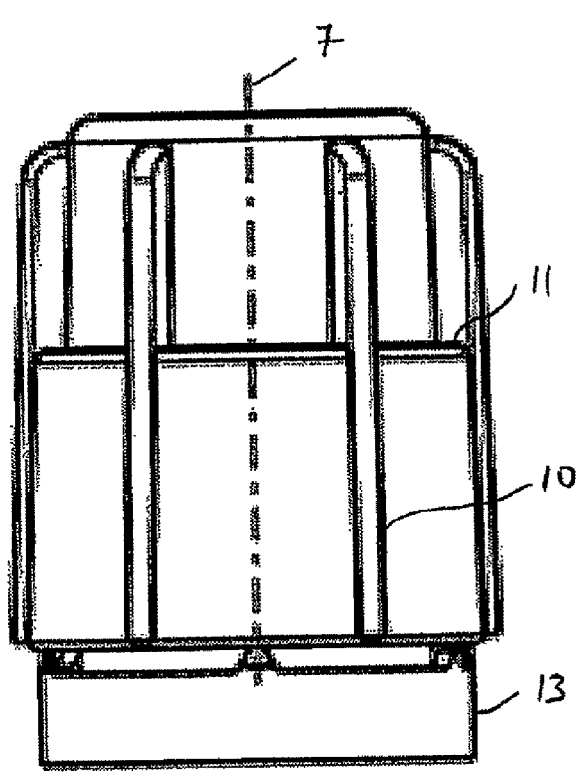
FIG..5
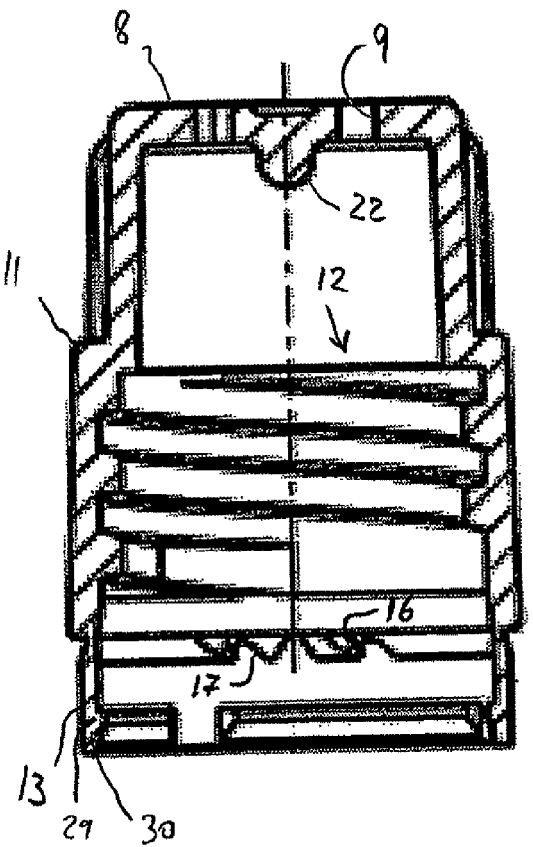
FIG..6

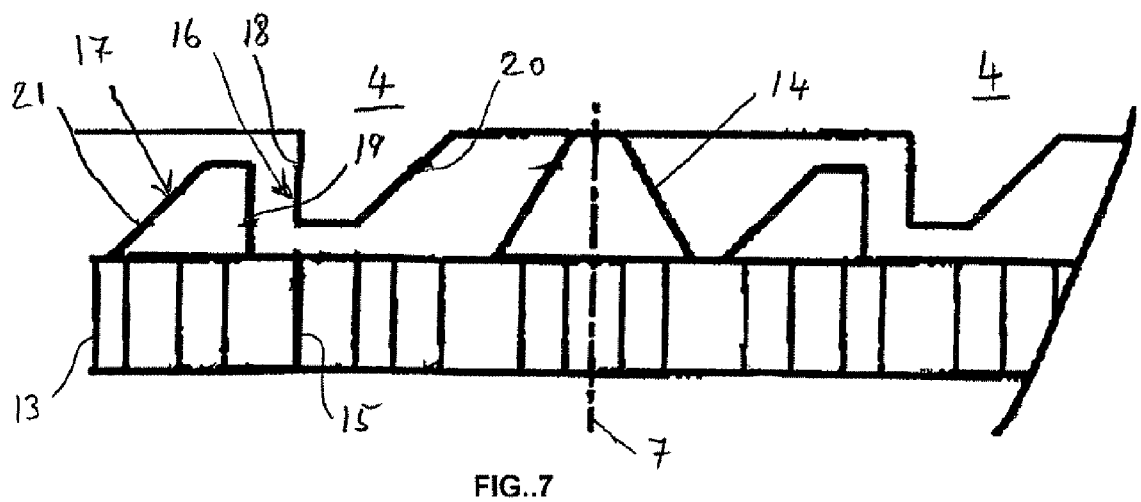
FIG..7
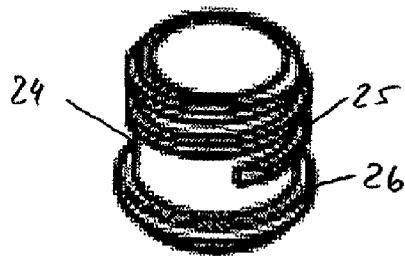
FIG..8
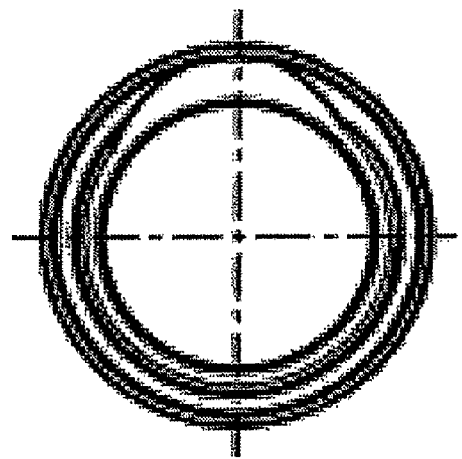
FIG..9
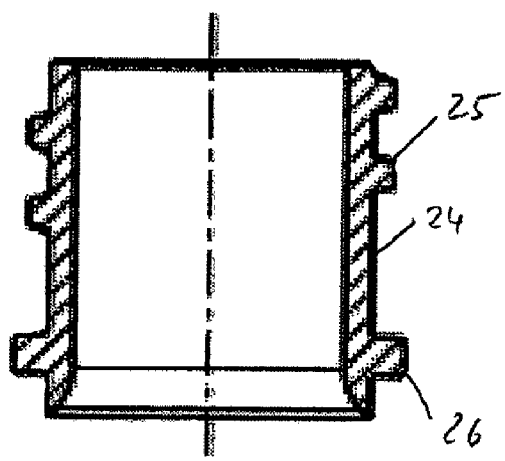
FIG..10
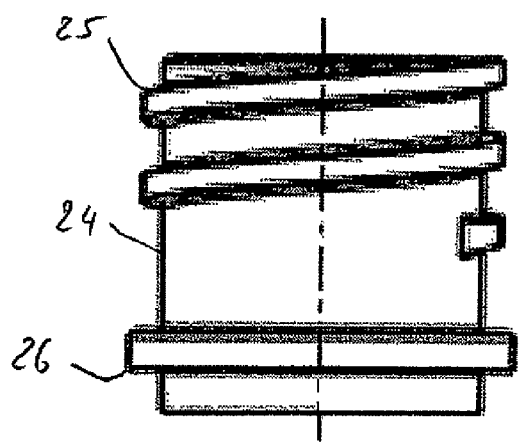
FIG..11

CLOSURE PIECE FOR MEDICAL SYRINGE

The present invention relates to a closure piece for a medical syringe.

DE 199 56 243 A1 discloses a medical syringe having a syringe barrel and a syringe neck connected to a distal end thereof. A closure cap can be fitted onto the syringe neck. A sleeve is provided around the closure cap. The closure cap with the sleeve can be inserted into an outer cap. The outer cap has a predetermined breaking point, such that a distal part of the outer cap can be removed, while a proximal part of the outer cap remains on the syringe. The closure cap can accordingly be removed and the syringe then used. The proximal part remaining on the syringe indicates that the syringe has been opened.

It is the object of the present invention to provide a closure piece for a medical syringe, wherein it can be ascertained whether the closure piece has been opened, which closure piece should be able to be used on a plurality of different syringes.

This object is achieved by a closure piece for a medical syringe according to claim 1.

Further developments of the closure piece are specified in the dependent claims.

A medical syringe with such a closure piece is likewise provided.

The adapter, which is to be fitted onto the syringe neck, enables the closure piece to be fitted onto a plurality of medical syringes. In particular, it is not required to provide an outer thread on the syringe neck onto which the screw-type closure piece can be screwed.

The screw-type closure piece and the twist-off ring preferably have projections serving as pickup catches. The connectors serve as tear-off connectors. The pickup catches can carry along the twist-off ring when being screwed on. If the closure piece is twisted off the connectors tear and the catches have no function.

The edges of the projections facing one another are preferably aligned in the longitudinal direction of the syringe, whereas the edges averted from one another are inclined relative to the longitudinal direction of the syringe. This ensures proper pickup function during screwing on, whereas with unscrewing, when the connectors tear, the projections can glide over one another.

The screw-type closure piece is preferably provided with a cover plate. The cover plate holds the closure cap, even when the syringe is subjected to external negative pressure e.g. during air transport. The cover plate holds the closure cap whenever the syringe is treated with superheated water or water vapor for sterilizing, with excess pressure building up inside the syringe.

Opening segments are preferably formed in the cover plate. The opening segments allow control when the closure cap is present, the opening segments enable intensive water exchange during autoclaving, and the opening segments enable the closure cap to be supported with a counter pressure ram during in-process control. Finally, the opening segments enable a rotary tool to be introduced to screw the screw-type closure piece on and off.

Further characteristics and practical applications of the invention will emerge from the following description of an embodiment by means of the figures, in which:

FIG. 1 is an overall view of a medical syringe;

FIG. 2 is a cross-sectional view of a syringe neck of the medical syringe with an inserted closure cap, with a fitted adapter and a screw-type closure piece;

FIG. 3 is a perspective view of the screw-type closure piece;

FIG. 4 is a plan view of the screw-type closure piece;

FIG. 5 is a side elevation of the screw-type closure piece;

FIG. 6 is a cross-sectional view of the screw-type closure piece;

FIG. 7 is an enlarged illustration of connectors and projections on the screw-type closure piece;

FIG. 8 is a perspective view of the adapter;

FIG. 9 is a plan view of the adapter;

FIG. 10 is a cross-sectional view of the adapter; and

FIG. 11 is a side elevation of the adapter.

FIG. 1 shows a medical syringe with a fitted closure piece as per an embodiment of the present invention. The end shown in the figure at the bottom points in the proximal direction, while the end shown in the figure at the top points in the distal direction. The terms "proximal" and "distal" are used in the following description to designate these directions.

As shown in FIG. 1, a closure piece or closure arrangement 1 is set on a needle shoulder, not shown in FIG. 1. The needle shoulder is connected to a syringe barrel 3 via a syringe shoulder 2. A plunger (not shown) is introduced into the syringe barrel 3 from the proximal end. The plunger serves to seal off the proximal end and as it is moved into the syringe barrel 3 it serves to dispense the medium contained in the syringe through the needle shoulder and a needle, not shown here.

As is best seen in FIG. 2, the closure piece 1 substantially comprises three components. The closure piece 1 comprises a screw-type closure piece 4, a closure cap or plug 5 and an adapter 6.

The screw-type closure piece 4 will be described herein below with reference to FIGS. 2 to 7. The screw-type closure piece 4 has a cup shape, open to the proximal end. The screw-type closure piece 4 is formed substantially rotationally symmetrical about its longitudinal axis 7. Formed on the upper side integrally with the screw-type closure piece 4 and opposite the proximal end of the screw-type closure piece 4 is a cover plate 8. The cover plate 8 has longitudinal holes 9, substantially in the shape of an arc of a circle. The purpose of the longitudinal holes 9 is to introduce a rotary tool. Further, the longitudinal holes 9 permit inspection of the closure cap 5. In case the syringe is to be autoclaved for terminal sterilisation the longitudinal holes 9 allow hot water and water vapor to be admitted to the closure cap or plug 5. To increase its mechanical strength the screw-type closure piece 4 is provided with a plurality of fins 10 extending on the outside in the direction of the longitudinal axis.

The screw-type closure piece has a widened screw section 11 at its proximal end. As is evident from FIG. 6, the screw section 11 is provided with an inner thread 12. As is best apparent from FIG. 7 a twist-off portion of the closure piece 4 in the form of a twist-off ring 13 is connected via connectors 14 to the actual screw-type closure piece 4. The connectors 14 exhibit a trapezoid shape, which is formed symmetrically to the longitudinal axis 7 of the screw-type closure piece 4. The twist-off ring 13 has fluting 15 peripherally enclosing the twist-off ring 13. Provided at the lower proximal end of the screw-type closure piece 4 are first projections 16, while second projections 17 are provided at the upper distal end of the twist-off ring 13. As is evident in particular from FIG. 7, in each case a first projection 16 of the screw-type closure piece 4 is formed adjacent to a second projection 17 of the twist-off ring 13. The edge 18 of the first projection 16, pointing to the second projection 17, extends substantially in the direction of the longitudinal axis 7 of the screw-type closure piece 4. The edge 19 of the second projection 17, pointing to the first projection 16, extends substantially in the direction of the longitudinal axis 7 of the screw-type closure piece 4. By comparison, the edge 20 of the first projection 16, averted from the second projection 17, is inclined relative to the longitudinal axis 7 of the screw-type closure piece 4, as shown in FIG. 7. The edge 21 of the second projection 17, averted from the first projection 16, is inclined relative to the longitudinal axis 7 of the screw-type closure piece 4, as shown in FIG. 7.

The first and second projections 16 and 17 form cooperating one-way rotation blocking surfaces on the closure piece 4 and the twist-off portion 13 which allow the closure piece 4 to rotate with respect to the twist-off portion 13 when unscrewed from the adaptor 6.

As best seen in FIG. 6, a projection in the form of a spherical bead 22 is provided on the inside of the cover plate 8. As shown in FIG. 2, the spherical bead 22 cooperates with the closure cap or plug 5. In particular, the spherical bead 22 presses on the closure cap 5 to hold the closure cap 5 in the syringe neck 23. Whenever the screw-type closure piece 4 is screwed on, the spherical bead 22 contacts the closure cap 5 over a small surface only. The rotary motion of the screw-type closure piece 4 therefore exerts practically no torque on the closure cap 5.

Next, the adapter 6 is described with reference to FIGS. 2 and 8 to 11. The adapter 6 is formed from a cylinder 24. The cylinder 24 is open on the top side and the underside. An outer thread 25 is formed at the distal end of the cylinder 24. A flange 26 is formed at the proximal end of the cylinder 24. The closure cap 5 is now described with reference to FIG. 2. The closure cap 5 is substantially cup-shaped. The closure cap 5 can be inserted into the syringe neck 23. The inside of the syringe neck 23 is formed by an inwards-protruding wall 27 with a groove 18 for taking up the closure cap 5 to better fasten the closure cap 5.

When using the closure piece, the adapter 6 is first attached to the syringe neck 23. The adapter 6 can be fitted on the syringe neck 23 and welded. Suitable procedures are laser welding, ultrasound, microwave or adhesion processes. The adapter 6 thus enables a syringe to be provided which has a thread 25 on its syringe neck 23. The adapter 6 enables those syringes to be used which have no outer thread on the syringe neck in terms of production, though a closure piece may be screwed on. The adapter 6 accordingly offers the option of using syringes to a larger extent than was previously the case.

After the adapter 6 is set on the syringe neck 23, the closure cap 5 is introduced to the syringe neck 23 to close the syringe neck 23.

Then the screw-type closure piece 4 is screwed onto the adapter 6. As the screw-type closure piece 4 is being screwed on, the projections 16 take along the projections 17 on the twist-off ring 13 on the screw-type closure piece 4. The screw-type closure piece 4 can therefore be screwed onto the adapter 6 along with the twist-off ring 13. At the end of the screwing-on procedure an inner projection 29 at the proximal end of the twist-off ring 13 with a bevel 30 comes over the flange 26 of the adapter 6, in the process locking the inner projection 29 under the flange 26 to prevent axial removal of the twist-off portion 13 when the closure piece 4 is removed.

When the syringe is being used, the screw-type closure piece 4 is turned in the opposite direction. The projections 16 of the screw-type closure piece 4 slide over the projections 17 of the twist-off ring 13. The connectors 14 tear. The screw-type closure piece 4 can be unscrewed from the adapter 6. The twist-off ring 13 remains on the syringe neck 23 and is prevented from falling down by the flange 26. At this point the closure cap 5 is removed from the syringe neck 23. If necessary, a needle (not shown) is set on the syringe neck. The syringe is ready for use.

The twist-off ring 13 held by the flange 26 of the adapter 6 indicates that a factory-applied screw-type closure piece has been removed. In this way the screw-type closure piece 4 and the twist-off ring 13 create a tamper-evident closure.

LEGEND 1 closure piece
2 syringe shoulder
3 syringe barrel
4 screw-type closure piece
5 closure cap
6 adapter
7 longitudinal axis
8 cover plate
9 opening segments or respectively longitudinal holes
10 fins
11 screw section
12 inner thread
13 twist-off ring
14 connectors
15 fluting
16 projections
17 second projections
18+19 edge
20+21 edge
22 spherical indentation
23 syringe neck
24 cylinder
25 outer thread
26 flange
27 projecting wall
28 inner projection
29 inner projection
30 bevel

The invention claimed is:

1. Closure piece (1) for a medical syringe having a syringe barrel (3) and a syringe neck (23) connected to a distal end thereof, with an adapter (6) which can be fitted onto the syringe neck (23), a screw-type closure piece (4) which can be fitted onto the adapter (6), a twist-off ring (13) connected to the screw-type closure piece (4), and a closure cap (5) which can be introduced into the syringe neck (23), in which the screw-type closure piece (4) and the twist-off ring (13) are connected to one another spaced apart by connectors (14), and first projections (16) extending to the twist-off ring (13) are provided on the screw-type closure piece (4) and second projections (17) extending to the screw-type closure piece (4) on the twist-off ring (13) are provided adjacent to the first projections (16), and in which the edge (18, 19) of a projection (16, 17), facing the adjacent projection (17, 16), extends substantially in the direction of the longitudinal axis (7) of the screw-type closure piece (4) and the edge (20, 21) of a projection (16, 17), averted from the adjacent projection (17, 16), is inclined relative to the longitudinal axis (7) of the screw-type closure piece (4).

2. Closure piece according to claim 1, in which the adapter (6) has an outer thread (25) at its distal end and the screw-type closure piece (4) has a complementary inner thread (12).

3. Closure piece according to claim 1, in which the adapter (6) has a flange (26) at its proximal end.

4. Closure piece according to claim 1, in which the connectors (14) have a trapezoid form symmetrical to the longitudinal axis (7) of the screw-type closure piece (4).

5. Closure piece according to claim 1, in which the screw-type closure piece (4) has a cover plate (8).

6. Closure piece according to claim 5, in which opening segments (9) are formed in the cover plate (8) for introducing a rotary tool and/or for exposing the closure cap (5).

7. Closure piece according to claim 5, in which a spherical bead (22) for pressing the closure cap (5) is formed on the inside of the cover plate (8).

* * * * *